US010869815B1

(12) United States Patent
Jones

(10) Patent No.: US 10,869,815 B1
(45) Date of Patent: Dec. 22, 2020

(54) SNEEZE BAG SYSTEM

(71) Applicant: Carey Leon Jones, Hemet, CA (US)

(72) Inventor: Carey Leon Jones, Hemet, CA (US)

(*) Notice: Subject to any disclaimer, the term of this patent is extended or adjusted under 35 U.S.C. 154(b) by 181 days.

(21) Appl. No.: 15/205,470

(22) Filed: Jul. 8, 2016

Related U.S. Application Data

(63) Continuation-in-part of application No. 14/659,490, filed on Mar. 16, 2015, now abandoned.

(60) Provisional application No. 62/075,374, filed on Nov. 5, 2014.

(51) Int. Cl.

| | |
|---|---|
| ***A61B 19/00*** | (2006.01) |
| ***A61J 19/00*** | (2006.01) |
| ***B65D 30/10*** | (2006.01) |
| ***B65D 65/46*** | (2006.01) |
| ***B65D 30/08*** | (2006.01) |
| ***B65D 33/00*** | (2006.01) |
| ***B65D 33/01*** | (2006.01) |

(52) U.S. Cl.
CPC .............. *A61J 19/00* (2013.01); *B65D 31/04* (2013.01); *B65D 31/16* (2013.01); *B65D 33/001* (2013.01); *B65D 33/01* (2013.01); *B65D 65/466* (2013.01); *A61J 2200/60* (2013.01)

(58) Field of Classification Search
CPC .......... B65D 33/00; A41B 15/00; A61J 19/00; A61J 19/02; A41D 13/11; A41D 13/1192; A41D 2400/34; A41D 2400/52; A41D 13/1107; A41D 13/1138; A41D 13/1146; A41D 13/1153; A61M 16/00; A61M 16/06; A61M 16/0003
USPC .......................................................... 128/863
See application file for complete search history.

(56) References Cited

U.S. PATENT DOCUMENTS

| | | | | |
|---|---|---|---|---|
| 7,947,024 B2 * | 5/2011 | Ramage | .................. | A61J 19/00 604/317 |
| 2004/0141663 A1 * | 7/2004 | Gillis | ...................... | A61J 19/00 383/42 |
| 2005/0261644 A1 * | 11/2005 | Fields | ..................... | A61J 19/00 604/317 |
| 2007/0298086 A1 * | 12/2007 | Deal | ....................... | A61J 19/00 424/443 |
| 2016/0325067 A1 * | 11/2016 | Harwood | .......... | A61M 16/0683 |

* cited by examiner

*Primary Examiner* — Victoria J Hicks
(74) *Attorney, Agent, or Firm* — Bruce A. Lev

(57) ABSTRACT

A pathogen-catching bag system includes a pathogen-catching bag assembly having a bag body formed from a flexible material and including a top edge having an opening therethrough, a bottom-edge, a left-edge, a right-edge, an exterior surface, an inner surface having a pathogen neutralizing lining, an inner-volume, and a nozzle portion connected to the top edge and opening and is adapted to fit snugly around a user's nose and mouth forming an air-tight seal. The pathogen-catching bag system permits the user to keep the sneeze confined to the pathogen-catching bag assembly thereby preventing transmittal of the pathogens into ambient-air thereby lowering transmission of colds and other viruses transmitted by sneezing to public areas.

19 Claims, 7 Drawing Sheets

SNEEZE BAG SYSTEM

CROSS-REFERENCE TO RELATED APPLICATION

The present application is related to and claims priority from prior provisional application Ser. No. 62/075,374, filed Nov. 5, 2014 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of disposable bags and more specifically relates to a pathogen-catching bag system.

2. Description of the Related Art

A sneeze is a semi-autonomous, convulsive expulsion of air from the lungs through the nose and mouth, usually caused by foreign particles irritating the nasal mucosa. A sneeze expels air forcibly from the mouth and nose in an explosive, spasmodic involuntary action resulting chiefly from irritation of the nasal mucous membrane. Sneezing is possibly linked to sudden exposure to bright light, sudden change in temperature, breeze of cold air, a particularly full stomach, or viral infection, and can lead to the spread of disease.

The function of sneezing is to expel mucus containing foreign particles or irritants and cleanse the nasal cavity. During a sneeze, the soft palate and palatine uvula depress while the back of the tongue elevates to partially close the passage to the mouth so that air ejected from the lungs may be expelled through the nose. Because the closing of the mouth is partial, a considerable amount of this air is usually also expelled from the mouth. The force and extent of the expulsion of the air through the nose varies.

Unfortunately, while our own sneeze may help to keep us healthy and sniffle-free, the bacteria and viruses that we remove by sneezing—up to 100,000 germs per sneeze, traveling at up to 100 miles per hour—represent a real microbial threat to the people around us. And if we politely cover our mouths and noses with our hands, we only transmit the germs there, to be left on the next door-handle we touch, or the next hand we shake. Thus, while the sneeze may be intended to help us individually, what really happens is that we get rid of germs that then pose a hazard to everyone else. This is not desirable.

Various attempts have been made to solve problems found in disposable bags art. Among these are found in: U.S. Pub. No. 2005/0045186 to Gary Takowsky; U.S. Pub. No. 2007/0298086 to Walter Ray Deal; U.S. Pat. No. 5,864,883 to Patricia M. Reo; and U.S. Pat. No. 7,997,275 to Michael Quinn. This prior art is representative of disposable containers for a user to sneeze or cough into and dispose of after use. None of the above inventions and patents, taken either singly or in combination, is seen to describe the invention as claimed.

Ideally, a pathogen-catching bag system should be user-friendly and safe in-use and, yet may operate reliably and be manufactured at a modest expense. Thus, a need exists for a pathogen-catching bag system for providing a user with a discreet and effective means of catching, containing, and neutralizing a sneeze so that germs expelled from a mouth and a nose of the user such that they are neither broadcast into the ambient air, nor transferred to a hand and arm of the user and to avoid the above mentioned problems.

BRIEF SUMMARY OF THE INVENTION

In view of the foregoing disadvantages inherent in the disposable bag device art, the present invention provides a pathogen-catching bag system (entitled 'The Sneeze Bag System'). The general purpose of the present invention, which will be described subsequently in greater detail is to provide a pathogen-catching bag system for providing a user with a discreet and effective means of catching, containing, and neutralizing a sneeze so that germs expelled from a mouth and a nose of the user such that they are neither broadcast into the air, nor transferred to a hand and arm of the user, thereby promoting public health.

A pathogen-catching bag system is disclosed herein comprising: a pathogen-catching bag assembly having a bag body including a top-edge, a bottom-edge, a left-edge, a right-edge, an exterior surface, an inner surface having a pathogen neutralizing lining, and an inner-volume. The pathogen-catching bag system comprises the pathogen-catching bag assembly. The pathogen-catching bag system permits the user to keep the sneeze confined to the pathogen-catching bag assembly thereby preventing transmittal of the pathogens into ambient-air thereby lowering transmission of colds and other viruses transmitted by sneezing to public areas.

The parameters of the bag body comprise a top-edge; the bottom-edge; the left-edge; the right-edge; the exterior surface; the inner surface having the pathogen neutralizing lining; and the inner-volume. The exterior surface and the inner surface define the inner-volume, the inner-volume suitable for containing and trapping the pathogens while preventing spreading of the pathogens to other users therein. The pathogen comprises at least one foreign bacteria micro-organism.

The pathogen-catching bag assembly is balloon-shaped thereby accommodating convulsive expulsion of air from through a nose and a mouth during sneeze. The pathogen-catching bag assembly is approximately 3-inches in diameter at the top edge. The top edge of the pathogen-catching bag assembly is positionable over a nose and a mouth of a user prior to the user sneezing to contain the pathogens from being uncontrollably expelled from the nose and the mouth. The pathogen-catching bag assembly is approximately 8-inches in depth when in the in-use condition during the sneeze. The pathogen-catching bag assembly is approximately 8-inches in diameter at a bottom portion when in the in-use condition during the sneeze. The pathogen-catching bag assembly is re-useable after one use of catching of the bacteria and the virus during the sneeze (our cough) from the mouth and the nose of the user.

The exterior surface of the bag body preferably comprises sanitary and soft paper. The sanitary and soft paper is absorbent and biodegradable. The sanitary and soft paper is impermeable thereby trapping in the pathogens once soiled from the sneezing. The sanitary and soft paper is flushable down a toilet bowl thereby being biodegradable.

The pathogen neutralizing lining located on the inner surface of the bag body is anti-microbial. The pathogen neutralizing lining located on the inner surface of the bag body may comprise alcohol. The inner surface having the pathogen neutralizing lining traps the expulsion from a mouth and a nose of the user when sneezing and neutralizes the sneeze contents while containing the pathogens in the pathogen-catching bag assembly. The pathogen-catching bag system is structured and arranged to provide the user with a discreet and effective means of catching, containing, and neutralizing the sneeze so that germs expelled from the mouth and the nose of the user such that they are neither broadcast into the air, nor transferred to a hand and arm of the user.

A kit is also embodied herein for the pathogen-catching bag system comprising: a plurality of at pathogen-catching bag assemblies stored in a multi-use pocket pack in a user-preferred color, design, shape and size; and a set of user instructions.

A method of using a surface pathogen-catching bag system comprises the steps of: choosing a pathogen-catching bag assembly in a user-preferred color, design, shape, and size; opening a storage pouch housing a plurality of the pathogen-catching bag assemblies; removing the pathogen-catching bag assembly from the storage pouch; placing the top edge of the pathogen-catching bag assembly over a mouth and a nose of a user prior to the user sneezing or coughing; the user imparting a sneeze and/or cough into the pathogen-catching bag assembly; and the user disposing of the pathogen-catching bag assembly once soiled with bacteria and viruses in a nearby receptacle after at least one sneeze and/or the cough.

The present invention holds significant improvements and serves as a pathogen-catching bag system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, pathogen-catching bag system (entitled the Sneeze Bag System) constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a disposable bag and more particularly to pathogen-catching bag system (also referred to herein as 'the Sneeze Bag System') to provide a pathogen-catching bag system for providing a user with a discreet and effective means of catching, containing, and neutralizing a sneeze so that germs expelled from a mouth and a nose of the user such that they are neither broadcast into the ambient air for others to breathe, nor transferred to a hand and arm of the user.

Generally speaking, the Sneeze Bag System comprises a specially designed personal hygiene accessory that anyone could carry in pocket or purse and use as needed to "catch" their sneeze—a disposable bag that may cover the mouth and nose during a sneeze, and catch and destroy bacteria and viruses within an antiseptic, impermeable lining.

The Sneeze Bag System may be produced in a variety of shapes, sizes, and colors to suit the size and aesthetic tastes of a variety of consumers, male and female, child and adult. In general, the Sneeze Bag System is preferably slightly balloon-shaped, with a diameter of approximately 3 inches at the top, a depth of approximately 8 inches, and a maximum bag-diameter of approximately 8 inches. The Sneeze Bag may be produced in a sanitary, soft, absorbent, flushable paper, and may feature an alcohol-based anti-microbial lining that preferably both absorb and kill bacteria and viruses released into the Sneeze Bag System. The outer layer of the Sneeze Bag System, in contrast, may be impermeable for use, but rapidly biodegradable when discarded or flushed. The Sneeze Bag System may be sold in handy, multi-unit pocket packs, similar to pocket tissues.

The user may simply place the open end of the Sneeze Bag System over his or her mouth and nose prior to a sneeze, then sneeze into the Bag, then twist the Bag shut as close to the mouth and nose as practicable. The Sneeze Bag System may be used and re-used on a limited basis, and disposed of in a trash can, or by flushing down a toilet. The Sneeze Bag System may provide individuals with a discreet and effective means of catching, containing, and indeed neutralizing a sneeze, so that the germs released are neither broadcast into the air, nor transferred to the covering hand or arm.

Thus, the Sneeze Bag System may enable the individual to keep his or her sneezes (and coughs, as well) from transmitting bacteria and viruses to others. Any reasonably polite and considerate consumer will preferably immediately see the good sense in this product, which may be so useful on public transportation, in schools, in restaurants, in health-care facilities, in short, anywhere that people are in relatively close quarters, where a sneeze or cough can most effectively spread germs to other people. As such, the Sneeze Bag System may have a dramatic effect in lowering the person-to-person transmission of colds and viruses which is desirable for public health.

Figure 1:
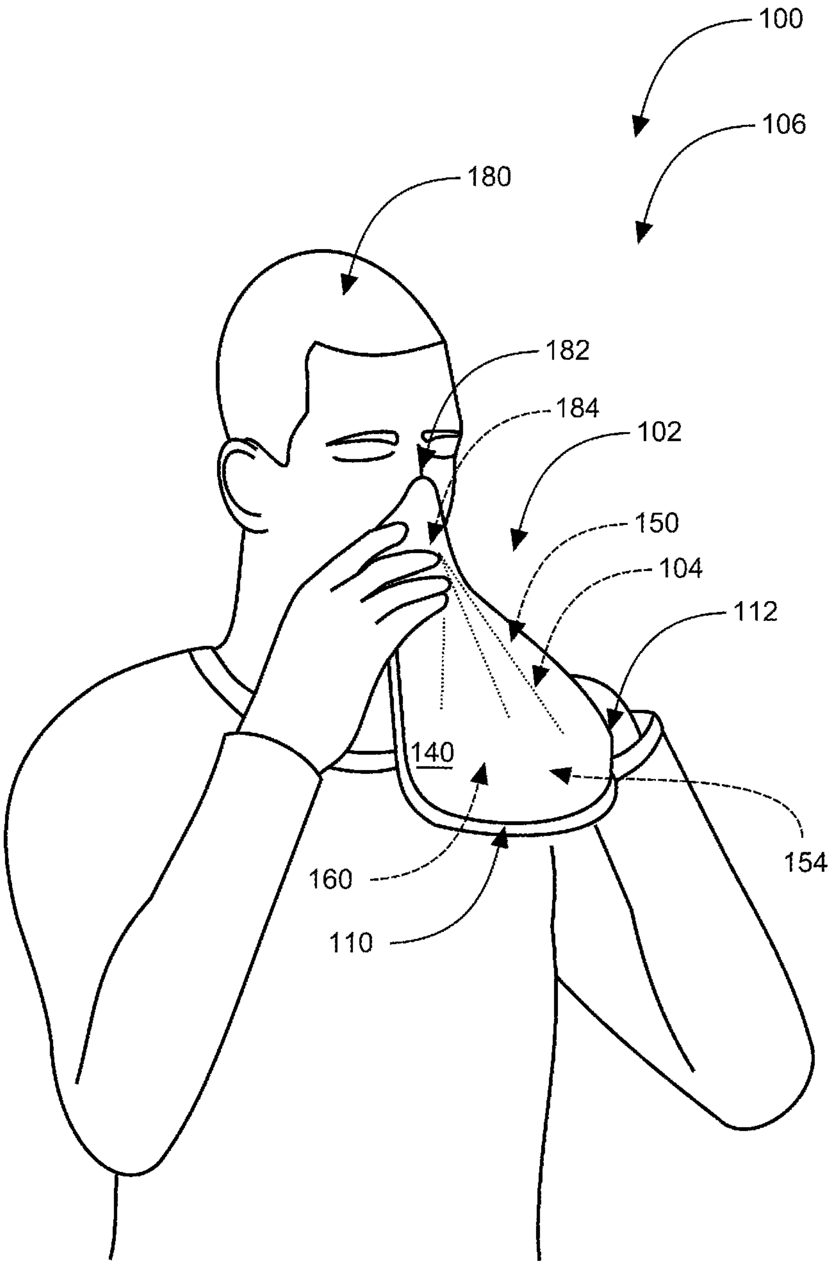
FIG. 1 shows a perspective view illustrating a pathogen-catching bag system in an in-use condition according to an embodiment of the present invention.
Figure 2:
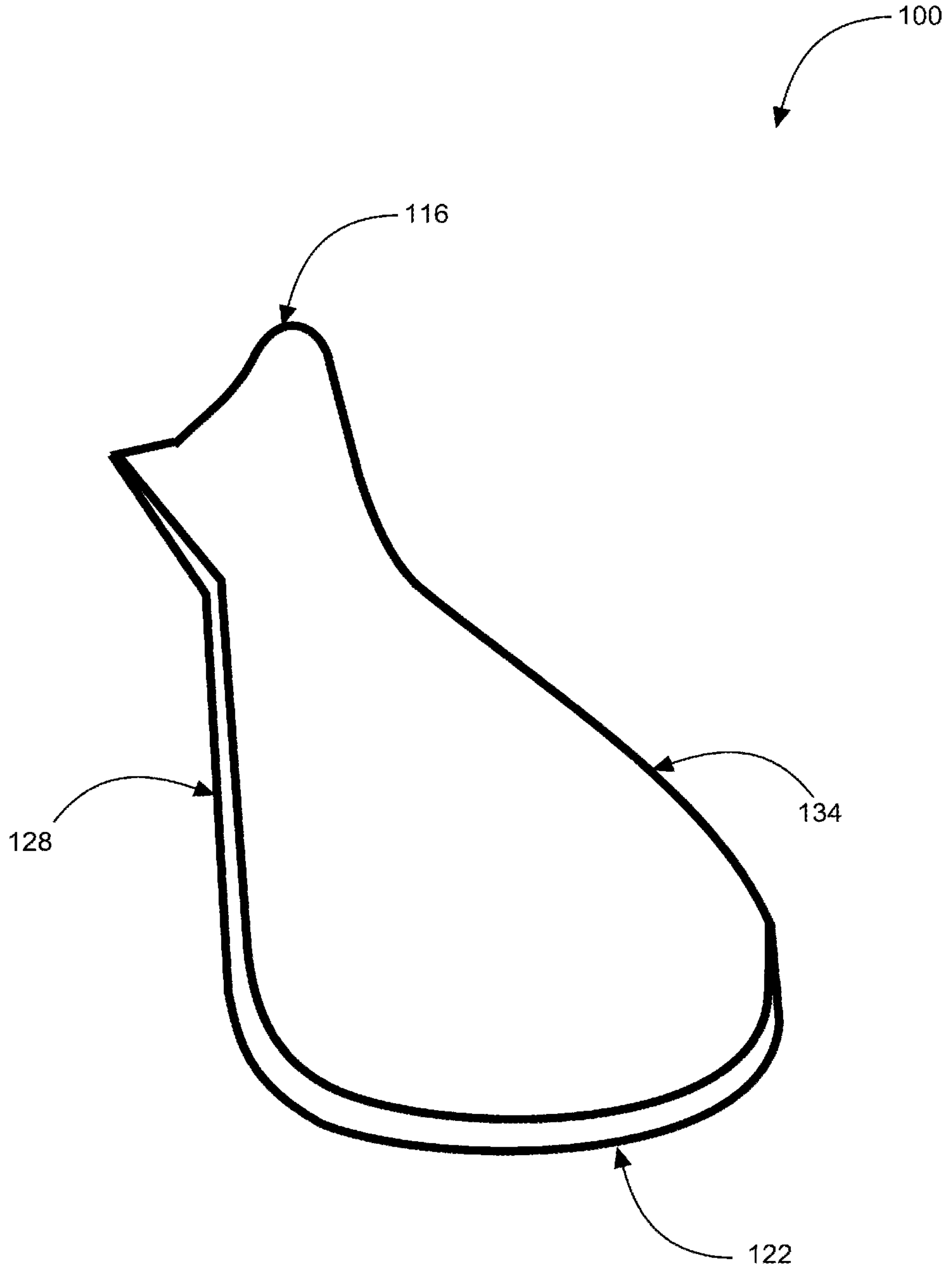
FIG. 2 is a front perspective view illustrating a pathogen-catching bag assembly of the pathogen-catching bag system according to an embodiment of the present invention of FIG. 1.
Figure 3:
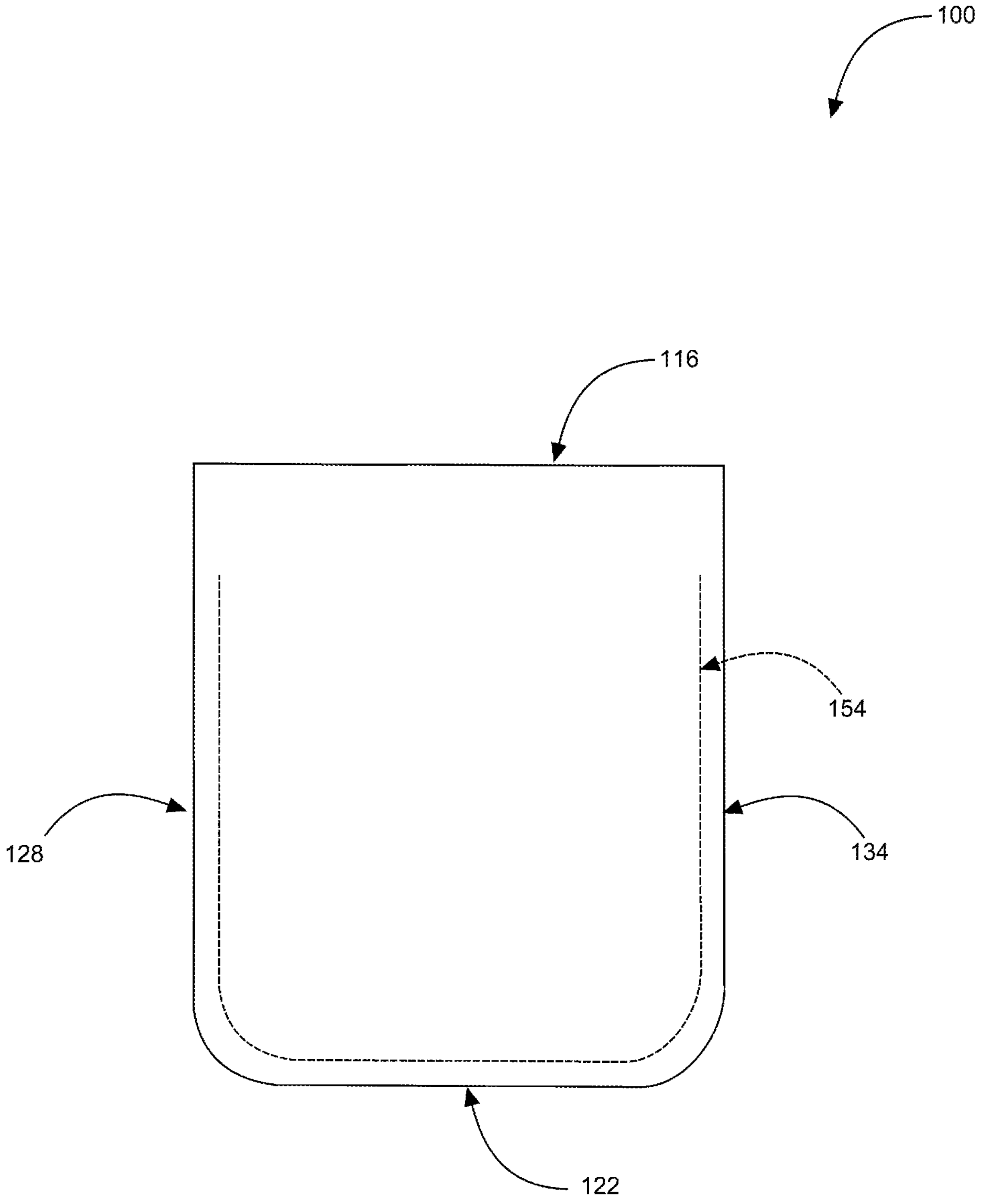
FIG. 3 is a front perspective view illustrating the pathogen-catching bag assembly of the pathogen-catching bag system according to an embodiment of the present invention of FIG. 1.

Referring now to the drawings by numerals of reference there is shown in FIGS. 1-3 perspective views illustrating pathogen-catching bag assembly 102 of pathogen-catching bag system 100 according to an embodiment of the present invention.

Pathogen-catching bag system 100 comprises: pathogen-catching bag assembly 102 having bag body 110 including a top-edge 116, bottom-edge 122, left-edge 128, right-edge 134, exterior surface 140, inner surface 150 having pathogen neutralizing lining 154, and inner-volume 160. Pathogen-catching bag system 100 comprises pathogen-catching bag assembly 102. Pathogen-catching bag system 100 permits user 180 to keep a sneeze confined to pathogen-catching bag assembly 104 thereby preventing transmittal of pathogens 104 into ambient-air thereby lowering transmission of colds and other viruses transmitted by sneezing to public areas as shown in in-use condition 106 of FIG. 1.

The parameters of bag body 110 comprise a top-edge 116; bottom-edge 122; left-edge 128; right-edge 134; exterior surface 140; inner surface 150 having pathogen neutralizing lining 154; and inner-volume 160. Exterior surface 140 and inner surface 150 define inner-volume 160, inner-volume 160 suitable for containing and trapping pathogens 104 while preventing spreading of pathogens 104 to other users 180 therein. Pathogen 104 comprises at least one foreign bacteria microorganism. Pathogen 104 may also comprise at least one foreign virus.

Pathogen-catching bag assembly 102 is 'balloon-shaped' 112 thereby accommodating convulsive expulsion of air from through nose 182 and mouth 184 during sneeze. Upon reading this specification, it should be appreciated that, under appropriate circumstances, considering such issues as user preferences, design preference, structural requirements, marketing preferences, cost, available materials, technological advances, etc., other shape arrangements such as, for example, rectangular, square, etc., may be sufficient.

Pathogen-catching bag assembly 102 is approximately 3-inches in diameter at top edge 116. The top edge 116 of pathogen-catching bag assembly 102 is positionable over nose 182 and mouth 184 of user 180 prior to user 180 sneezing to contain pathogens 104 from being uncontrollably expelled from nose 182 and mouth 184. Pathogen-catching bag assembly 102 is approximately 8-inches in depth when in in-use condition 106 during the sneeze. Pathogen-catching bag assembly 102 is approximately 8-inches in diameter at a bottom edge 122 when in in-use condition 106 during said sneeze. Pathogen-catching bag assembly 102 is re-useable after one use of catching of the bacteria and the virus during the sneeze from mouth 184 and nose 182 of user 180. In an alternate embodiment, pathogen-catching bag assembly 102 is disposable after one use of catching of the bacteria and the virus during the sneeze from mouth 184 and nose 182 of user 180.

The exterior surface of bag body 110 comprises sanitary and soft paper. The sanitary and soft paper is absorbent and biodegradable. The sanitary and soft paper is impermeable thereby trapping in the pathogens once soiled from the sneezing. The sanitary and soft paper is flushable down a toilet bowl thereby biodegradable.

The pathogen neutralizing lining located on the inner surface of bag body 110 is anti-microbial. The pathogen neutralizing lining located on the inner surface of bag body 110 comprises alcohol. The inner surface having the pathogen neutralizing lining traps the expulsion from a mouth and a nose of the user when said sneezing and neutralizes while containing said pathogens in said pathogen-catching bag assembly 102. Pathogen-catching bag system 100 is structured and arranged to provide the user with a discreet and effective means of catching, containing, and neutralizing sneezes so that germs expelled from said mouth and the nose of the user such that they are neither broadcast into the air, nor transferred to a hand and arm of the user.

Figure 4:
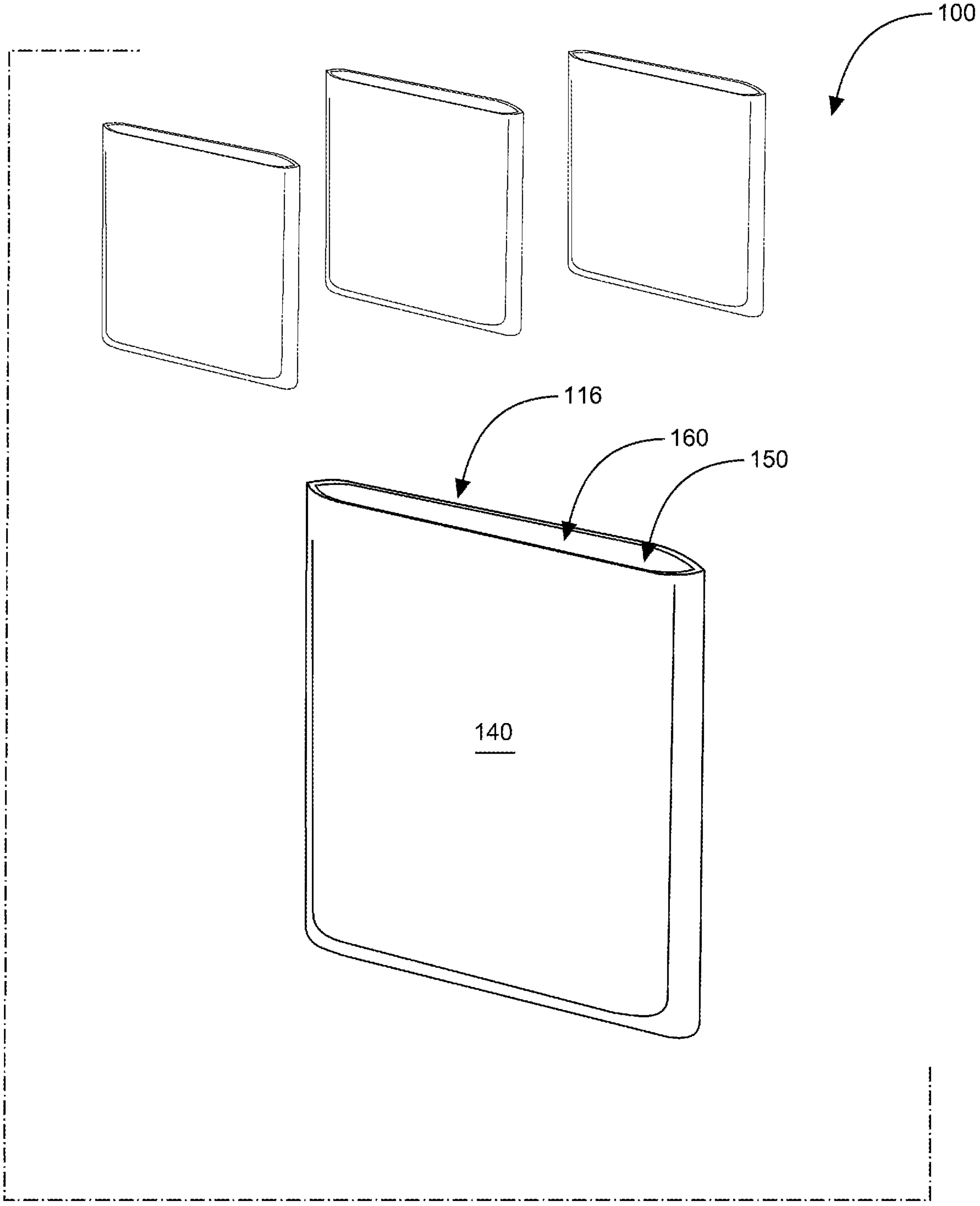
FIG. 4 is a perspective view illustrating a kit of pathogen-catching bag system according to an embodiment of the present invention.

Referring now to FIG. 4 showing a perspective view illustrating kit of pathogen-catching bag system 100 according to an embodiment of the present invention of FIG. 1

Kit is embodied herein for pathogen-catching bag system 100 comprises: a plurality of at pathogen-catching bag assemblies 102 stored in a multi-use pocket pack in a user-preferred color, design, shape and size; and a set of user-installation instructions.

The kit has instructions such that functional relationships are detailed in relation to the structure of the invention (such that the invention can be used, maintained, or the like in a preferred manner). Pathogen-catching bag system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 5:
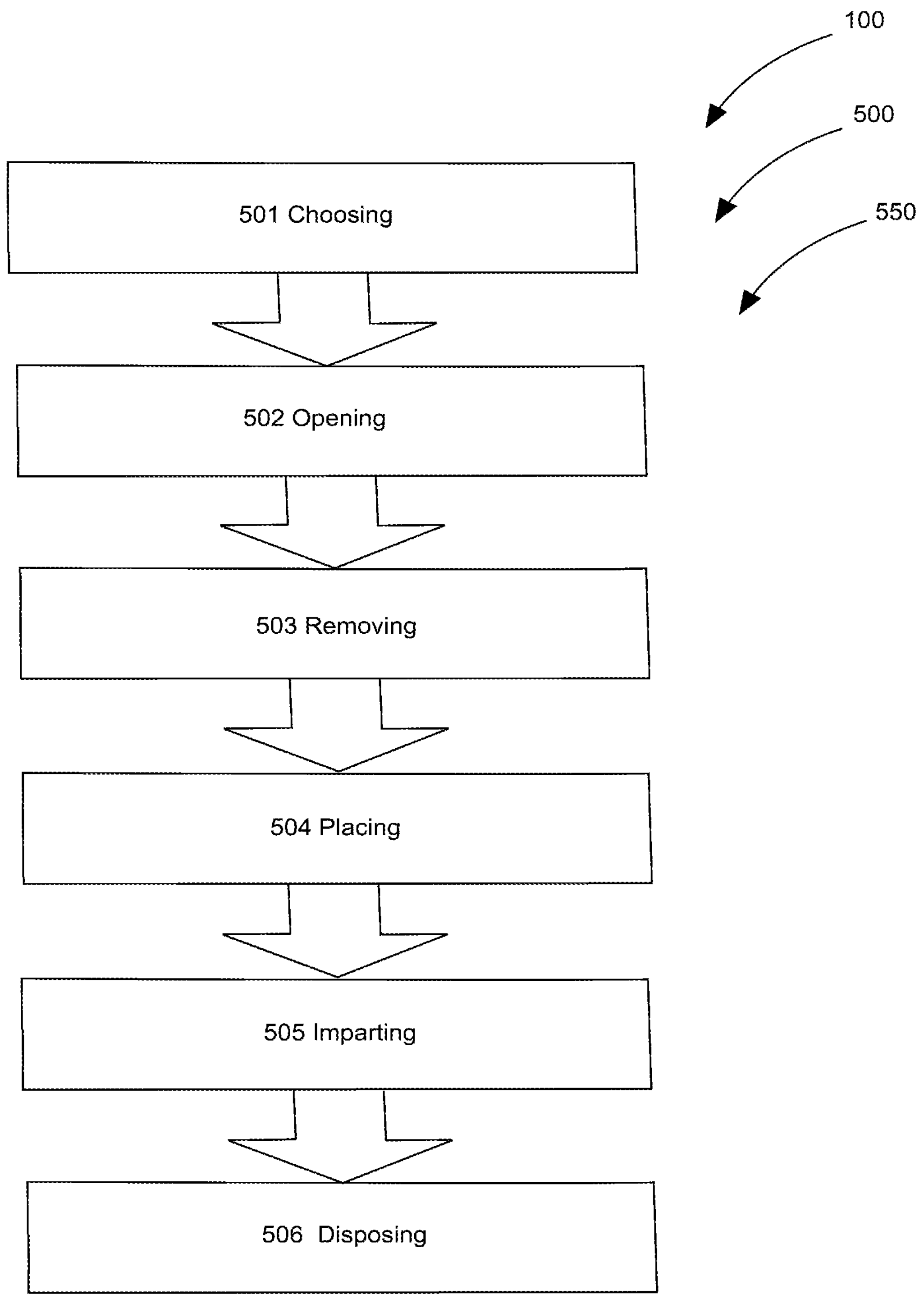
FIG. 5 is a flowchart illustrating a method of use for the pathogen-catching bag system according to an embodiment of the present invention of FIGS. 1-4.
Figure 6:
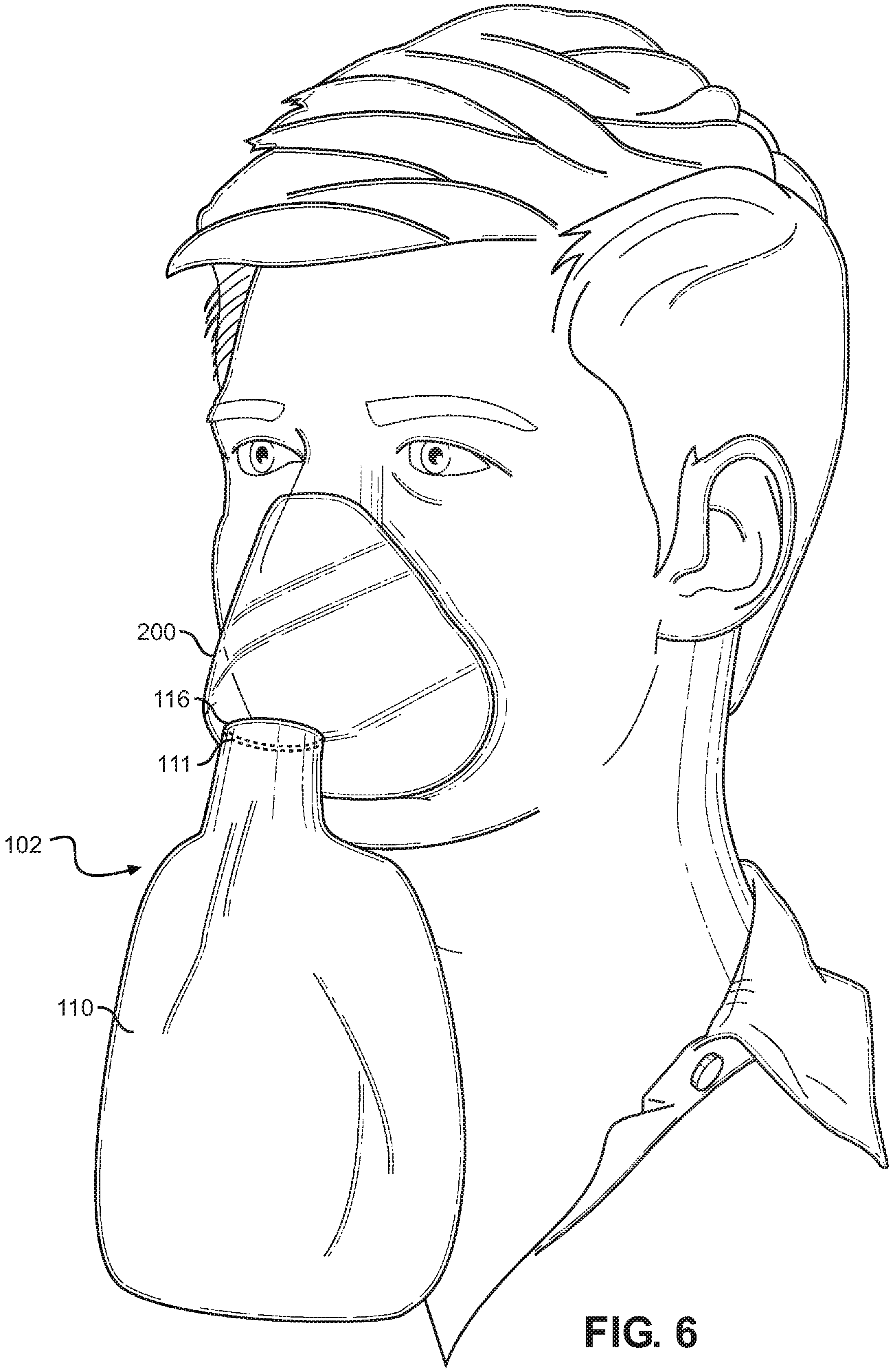
FIG. 6 illustrates a perspective view of an embodiment of the pathogen-catching bag system including a rigid nozzle member having sealing means for providing an air-tight seal between the nozzle member and a user's face.
Figure 7:
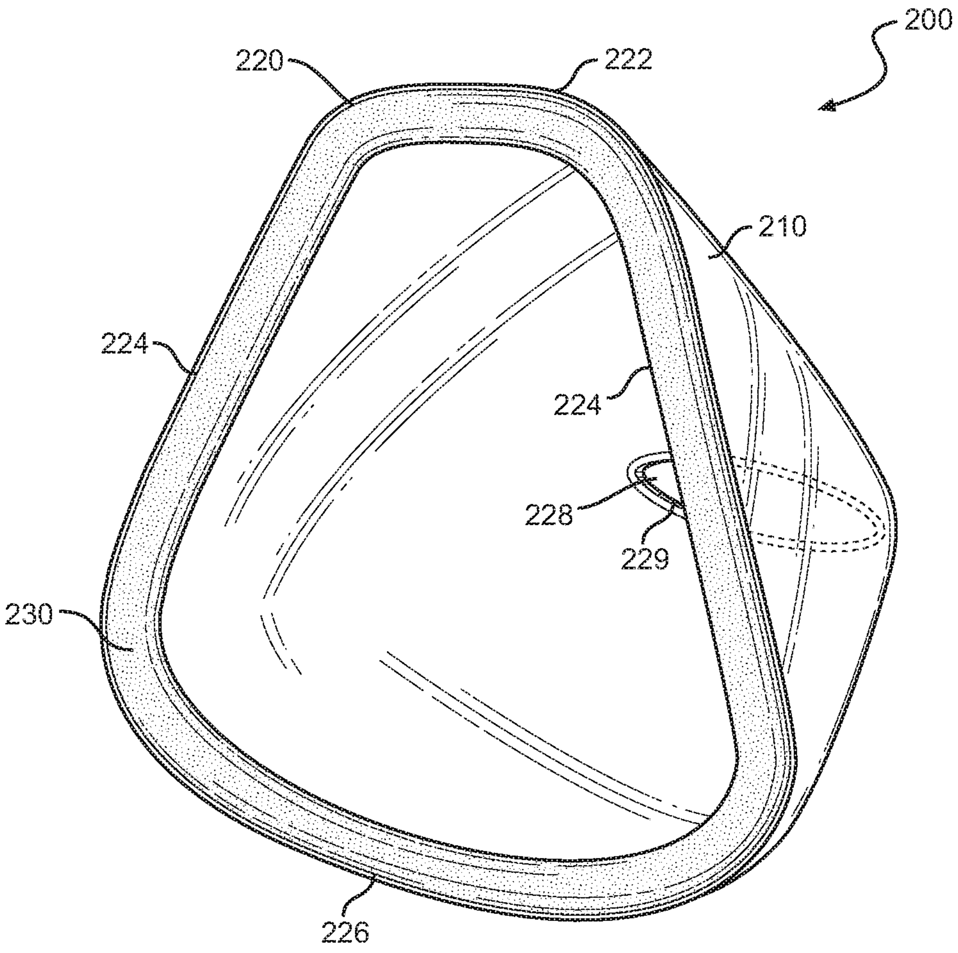
FIG. 7 illustrates a perspective view of the rigid nozzle member of FIG. 6 including the sealing means for providing an air-tight seal between the nozzle member and user's face.

Referring now to FIG. 5, flowchart 550 illustrating method of use 500 for pathogen-catching bag system is 100 according to an embodiment of the present invention of FIGS. 1-4.

Method of using (method of use 500) pathogen-catching bag system 100 comprises the steps of: step one 501 choosing a pathogen-catching bag assembly in a user-preferred color, design, shape, and size; step two 502 opening a storage pouch housing a plurality of said pathogen-catching bag assemblies; step three 503 removing said pathogen-catching bag assembly from said storage pouch; step four 504 placing the top edge of said pathogen-catching bag assembly over a mouth and a nose of a user prior to the user sneezing or coughing; step five 505 the user imparting a sneeze and/or cough into pathogen-catching bag assembly; and step six 506 the user disposing of said pathogen-catching bag assembly once soiled with bacteria and viruses after at least one said sneeze and/or said cough in a nearby receptacle.

It should be noted that the steps described in the method of use can be carried out in many different orders according to user preference. The use of "step of" should not be interpreted as "step for", in the claims herein and is not intended to invoke the provisions of 35 U.S.C. § 112, 16.

Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A pathogen-catching bag system comprising:
a pathogen-catching bag assembly having:
a bag body comprising:
a flexible material;
a top-edge;
wherein said top-edge forms an opening adapted to provide access into an inner-volume of said bag body;
a bottom-edge;
a left-edge;
a right-edge;
an exterior surface;
an inner surface having a pathogen neutralizing lining; and
a nozzle portion connected to said top-edge of said bag body,
said nozzle portion comprising:
a side wall;
wherein said side wall is formed from a rigid material; and
wherein said side wall tapers along its length forming a cone-shaped tube that is adapted to extend outwardly from a user's face when in use;
an open top portion located on a proximal end portion of said side wall and comprises:
a curved upper section adapted to fit upon and be pressed against the bridge of a user's nose;
two straight side sections respectively connected to and extending at equal opposite angles from opposite sides of said curved upper section to thereby form a flare-shape that is adapted to fit upon and be pressed against side portions of said bridge of said user's nose, along said user's face, and downwardly adjacent and past said user's mouth; and
a curved bottom section connected between said two straight side sections and adapted to fit upon and be pressed against an upper chin section of said user's face, to thereby be adapted to form an air-tight seal around said user's nose and mouth; and an open bottom portion located on a distal end portion of said side wall;
wherein said open bottom portion includes an edge connected to said top-edge of said bag body and thereby allow access therethrough and into said inner-volume of said bag body;
wherein said pathogen-catching bag system is adapted to permit said user to keep expelled pathogens confined to said pathogen-catching bag assembly thereby preventing transmittal of said pathogens into public areas.

2. The pathogen-catching bag system of claim 1 wherein said exterior surface of said bag body comprises sanitary paper.

3. The pathogen-catching bag system of claim 2 wherein said sanitary paper is absorbent and biodegradable.

4. The pathogen-catching bag system of claim 3 wherein said sanitary paper is flushable down a toilet bowl thereby biodegradable.

5. The pathogen-catching bag system of claim 2 wherein said sanitary paper is impermeable thereby being capable of trapping in pathogens once soiled from sneezing.

6. The pathogen-catching bag system of claim 1 wherein said pathogen neutralizing lining located on said inner surface of said bag body is anti-microbial.

7. The pathogen-catching bag system of claim 6 wherein said pathogen neutralizing lining located on said inner surface of said bag body comprises alcohol.

8. The pathogen-catching bag system of claim 6 wherein said pathogen neutralizing lining located on said inner surface of said bag body does not comprise alcohol.

9. The pathogen-catching bag system of claim 1, wherein said curved upper section, said two straight side sections, and said curved bottom section of said open top portion of said nozzle portion further include a material thereon adapted to provide improved sealing means between said nozzle portion and said user's face.

10. The pathogen-catching bag system of claim 9, wherein said material comprises rubber.

11. The pathogen-catching bag system of claim 9, wherein said material comprises compressible foam material.

12. The pathogen-catching bag system of claim 1 wherein said bag body is formed having a rectangular-shape.

13. The pathogen-catching bag system of claim 1 wherein said pathogen-catching bag assembly is formed having a balloon-shape.

14. The pathogen-catching bag system of claim 1 wherein said pathogen-catching bag assembly is disposable after one use of catching of said bacteria and said virus during said sneeze from said mouth and said nose of said user.

15. The pathogen-catching bag system of claim 1 wherein said pathogen-catching bag assembly is re-useable.

16. The pathogen-catching bag system of claim 1, further comprising a kit including: a plurality of said pathogen-catching bag assemblies stored in a multi-use pocket pack; and a set of user instructions.

17. The pathogen-catching bag system of claim 1, wherein said rigid material of said side wall of said nozzle portion is made from a plastic material.

18. The pathogen-catching bag system of claim 1, wherein said rigid material of said side wall of said nozzle portion is made from a cardboard material.

19. The pathogen-catching bag system of claim 1, wherein said rigid material of said side wall of said nozzle portion is made from a metallic material.

* * * * *